(12) United States Patent
Kushiki et al.

(10) Patent No.: US 7,883,878 B2
(45) Date of Patent: *Feb. 8, 2011

(54) DRY GRANULATED PRODUCT CONTAINING L-LYSINE AS MAIN COMPONENT

(75) Inventors: Takeshi Kushiki, Kawasaki (JP); Junko Morikawa, Kawasaki (JP); Kazuhiko Hasegawa, Yokkaichi (JP)

(73) Assignee: Ajinomoto Co., Inc., Tokyo (JP)

( * ) Notice: Subject to any disclaimer, the term of this patent is extended or adjusted under 35 U.S.C. 154(b) by 133 days.

This patent is subject to a terminal disclaimer.

(21) Appl. No.: 12/172,676

(22) Filed: Jul. 14, 2008

(65) Prior Publication Data

US 2009/0017507 A1    Jan. 15, 2009

Related U.S. Application Data

(63) Continuation of application No. 10/350,043, filed on Jan. 24, 2003, now Pat. No. 7,416,740.

(30) Foreign Application Priority Data

Jan. 25, 2002  (JP) ............................ 2002-017054

(51) Int. Cl.
C12P 13/08 (2006.01)
A61K 9/14 (2006.01)
A01N 37/12 (2006.01)

(52) U.S. Cl. ........................ 435/115; 424/489; 514/564
(58) Field of Classification Search ................ 435/115; 424/489; 514/564
See application file for complete search history.

(56) References Cited

U.S. PATENT DOCUMENTS

| 5,133,976 | A |   | 7/1992 | Rouy |   |
|---|---|---|---|---|---|
| 5,431,933 | A |   | 7/1995 | Binder et al. |   |
| 6,756,510 | B1 |   | 6/2004 | Binder et al. |   |
| 7,416,740 | B2 | * | 8/2008 | Kushiki et al. | 424/489 |
| 2002/0025564 | A1 |   | 2/2002 | Kobayashi et al. |   |

FOREIGN PATENT DOCUMENTS

| AT | E 29 198 B | 10/1984 |
| CZ | 275 097 | 8/1988 |
| EP | 0 491 638 A2 | 6/1992 |
| EP | 0 809 940 A2 | 12/1997 |
| EP | 0 923 878 | 6/1999 |
| EP | 0 923 878 A2 | 6/1999 |
| EP | 1 004 300 | 5/2000 |
| EP | 1 035 109 | 9/2000 |
| EP | 1 068 804 | 1/2001 |
| EP | 1 118 673 | 7/2001 |
| EP | 1 182 261 A1 | 2/2002 |
| GB | 849 370 | 9/1960 |
| GB | 1 439 121 | 6/1976 |
| JP | 62-104553 | 5/1987 |
| WO | 95/23129 | 8/1995 |

OTHER PUBLICATIONS

Steven R. Hull, et al., "Composition of Corn Steep Water during Steeping", J. Agric. Food Chem., vol. 44, 1996, pp. 1857-1863.
Biolys 60—Product Information, Degussa, 2 Pages, Apr. 1995.
General Report, Document No. 2003 / 2688, Report: Ionenbilanz Biolys, Degussa, Nov. 21, 2003, pp. 2-6.
Wolf-Dieter Deckwer, et al., "Biotechnologie und Gentechnik", Römpp Lexikon, 1999, 4 Pages.
Joseph J. Vallino, et al., "Metabolic Flux Distributions in *Corynebacterium glutamicum* During Growth and Lysine Overproduction", Biotechnology and Bioengineering, vol. 41, No. 6, Mar. 15, 1993, pp. 633-646.
P. W. Van Der Poel, et al., "Zuckertechnologie, Ruben- und Rohrzuckergewinnung", 1998. 5 Pages.
Speditionsaufträge, "Warehouse Move-Talke", Rechungskopien, Not Nrs.: BL01100292A/BL0008252.
Wulf Crueger, et al., "Lehrbuch der Angewandten Mikrobiologie", Akademische Verlagsgesellschaft Wiesbaden, 1982, 3 Pages.
"Handbook of *Corynebacterium glutamicum*", 2005, 14 Pages.
Frank Menkel, "Eiführung in die Technik von Bioreaktoren", 1992, 4 Pages.
Erwin Riedel, "Allgemeine und Anorganische Chemie", 1990, 7 Pages.
A. F. Holleman, et al., "Lehrbuch Der Anorganischen Chemie", 1964, 2 Pages.
Adrian Schumpe, et al., "Gas Solubilities in Microbial Culture Media", Advances in Biochemical Engineering/Biotechnology, vol. 24, 1982, 39 Pages.
Patent Abstracts of Japan, JP 09-028310, Feb. 4, 1997.
John A. Dean, Analytical Chemistry Handbook, 1995, McGraw-Hill, Inc. Table 14.32.

* cited by examiner

*Primary Examiner*—Robert A Wax
*Assistant Examiner*—Aradhana Sasan
(74) *Attorney, Agent, or Firm*—Oblon, Spivak, McClelland, Maier & Neustadt, L.L.P.

(57) ABSTRACT

Hydrochloric acid, sulfuric acid or an L-lysine solution having an equivalent ratio of anion/L-lysine higher than 0.95 is added to a raw material L-lysine solution having an equivalent ratio of anion/L-lysine lower than 0.68 to adjust the equivalent ratio of anion/L-lysine of the raw material solution to be in the range of 0.68 to 0.95, and the obtained L-lysine solution or a concentrate thereof is granulated and dried to obtain a dry granulated product having a high L-lysine content and showing low caking property and low hygroscopic property.

5 Claims, No Drawings

DRY GRANULATED PRODUCT CONTAINING L-LYSINE AS MAIN COMPONENT

CROSS-REFERENCE TO RELATED APPLICTIONS

The present application is continuation of U.S. Ser. No. 10/350,043, filed on Jan. 24, 2003, and claims priority to JP 2002-17054, filed on Jan. 25, 2002.

BACKGROUND OF THE INVENTION

1. Field of the Invention

The present invention relates to a dry granulated product containing L-lysine as a main component. L-lysine is useful as an additive for animal feed and so forth.

2. Description of the Related Art

Since an additive for animal feed containing an amino acid as a main component is not required to be purified so much when it is used as an additive for feed, it has been attempted to produce such an additive by directly drying a fermentation solution in which an amino acid is accumulated (Japanese Patent Laid-open Publication (Kokai) Nos. 59-169454 and 5-192089). According to Japanese Patent Laid-open Publication No. 5-192089, it is pointed out that, in additives for animal feed obtained in such a manner, free amino acid content is more reduced in a dry product containing a basic amino acid as a main component compared with a dry product containing a neutral amino acid as a main component. It is considered that this is caused partly because anions are added to a culture broth during the culture for the production of a dry product containing a basic amino acid as counter anions of the basic amino acid to maintain electric neutrality of the culture broth, and the presence of the anions in the dry product results in the reduction of the amino acid content. This problem is also observed for L-lysine, which is one of basic amino acids.

Use of crystals or dry product of L-lysine base not containing counter ions at all as an additive for animal feed may be conceived in order to improve L-lysine content in the solid matter. However, L-lysine base suffers from a problem that it shows marked hygroscopic property and caking property, and thus its handling is difficult.

As a method of improving hygroscopic property and caking property of a dry product, for example, a method of adding an anticaking agent is contemplated as disclosed in Japanese Patent Laid-open Publication No. 9-28310. However, addition of anticaking agent results in reduction of content in the final product and further it is also economically disadvantageous.

SUMMARY OF THE INVENTION

An object of the present invention is to provide a dry granulated product containing L-lysine, which has an L-lysine content improved by reducing counter ions in the dry L-lysine product and shows low hygroscopic property and low caking property.

The inventors of the present invention have made extensive studies in order to achieve the aforementioned object. As a result, they found that a dry granulated product containing L-lysine having a high L-lysine content and showing low hygroscopic property and low caking property could be obtained by adjusting an equivalent ratio of anion/L-lysine of a fermentation solution or a solution containing L-lysine obtained from a fermentation solution to be 0.68 to 0.95, granulating and drying the obtained solution. The inventors of the present invention further found that an amount of a source of counter anions such as sulfate ions can be reduced by using carbon dioxide generated during fermentation instead of the counter anions. The inventors of the present invention also found that a dry granulated product having a high L-lysine content and showing low hygroscopic property and low caking property could also be obtained by using the aforementioned method. The present invention was accomplished based on these findings and provides the followings.

(1) A dry granulated product containing L-lysine and having the following composition:
  L-lysine content in solid matter: 40 to 85% by weight
  equivalent ratio of anion/L-lysine: 0.68 to 0.95
  moisture content: 5% by weight or less wherein the equivalent ratio of anion/L-lysine is a value calculated in accordance with the following equation by using L-lysine (L-Lys) content, sulfate ion content, chloride ion content, ammonium ion content, sodium ion content, potassium ion content, magnesium ion content and calcium ion content in the solid matter of the dry granulated product:

$$\text{equivalent ratio of anion/L-lysine} = (2\times[SO_4^{2-}] + [Cl^-] - [NH_4^+] - [Na^+] - [K^+] - 2\times[Mg^{2+}] - 2\times[Ca^{2+}])/[\text{L-Lys}]$$

where [ ] means a molar concentration.

(2) A method for preparing a dry granulated product containing L-lysine and having the following composition:
  L-lysine content in solid matter: 40 to 85% by weight
  equivalent ratio of anion/L-lysine: 0.68 to 0.95
  moisture content: 5% by weight or less which method comprises the steps of adding hydrochloric acid, sulfuric acid or an L-lysine solution having an equivalent ratio of anion/L-lysine higher than 0.95 to a raw material L-lysine solution having an equivalent ratio of anion/L-lysine lower than 0.68 to adjust the equivalent ratio of anion/L-lysine of the raw material solution to be in the range of 0.68 to 0.95, and obtaining the dry granulated product from the obtained L-lysine solution or a concentrate thereof.

(3) The method according to (2), wherein the raw material L-lysine solution is obtained by loading an aqueous solution containing L-lysine on a cation exchange resin so that L-lysine should adsorb on the resin and eluting the L-lysine adsorbed on the resin with aqueous ammonia, aqueous ammonium chloride solution or both of these.

(4) The method according to (2) or (3), wherein the L-lysine solution having an equivalent ratio of anion/L-lysine higher than 0.95 is a fermentation solution in which L-lysine is accumulated.

(5) A method for preparing a dry granulated product containing L-lysine, comprising the steps of culturing a microorganism having an ability to produce L-lysine in a liquid medium under an aerobic condition to produce and accumulate L-lysine in the medium and obtaining the dry granulated product from the medium, wherein
  the culture is performed to obtain a fermentation solution containing L-lysine, while pH of the medium is controlled to be 6.5 to 9.0 during the culture and to be 7.2 to 9.0 at the end of the culture, and pressure in a fermentation tank is controlled to be positive during the culture, or carbon dioxide or a mixed gas containing carbon dioxide is supplied into the medium so that there should be a culture period where bicarbonate and/or carbonate ions are present in the medium in an amount of 2 g/L or more, if necessary, hydrochloric acid, sulfuric acid or an L-lysine solution having an equivalent ratio of anion/L-lysine higher than 0.95 is added to the fermentation solution so that the fermentation solution should have an equivalent ratio of anion/L-lysine in the range of 0.68 to 0.95, and the fermentation solution is concentrated under reduced pressure, and the obtained concentrate is granulated and dried to obtain a dry granulate product containing L-lysine and having the following composition:

L-lysine content in solid matter: 40 to 85% by weight
equivalent ratio of anion/L-lysine: 0.68 to 0.95
moisture content: 5% by weight or less.

PREFERRED EMBODIMENTS OF THE INVENTION

Hereafter, the present invention will be explained in detail.

The dry granulated product containing L-lysine of the present invention has the following composition.
(1) L-Lysine content in solid matter: 40 to 85% by weight
(2) equivalent ratio of anion/L-lysine: 0.68 to 0.95
(3) moisture content: 5% by weight or less Conventional dried granulated products containing L-lysine as a main component suffer from a problem of reduction of free L-lysine content. On the other hand, one of the features of the dry granulated product of the present invention is that a free L-lysine content is high while a high L-lysine content is maintained, since an excessive amount of anions as counter ions of L-lysine are absent. The L-lysine content of the dry granulated product of the present invention is 40 to 85%, preferably 50 to 85%, more preferably 60 to 85% by weight, based on the solid matter in the dry granulated product. Such an L-lysine content can be obtained by granulating and drying an L-lysine solution after the equivalent ratio of anion/L-lysine of the L-lysine solution described below is adjusted to a predetermined value.

A dry granulated product containing L-lysine in an amount in the range defined above can be obtained by adjusting the equivalent ratio of anion/L-lysine of an L-lysine fermentation solution or a raw material L-lysine solution collected from the L-lysine fermentation solution to be 0.68 to 0.95, preferably 0.68 to 0.90, more preferably 0.68 to 0.86, and obtaining a dry granulated product from the obtained L-lysine solution or a concentrate thereof.

In the present invention, the equivalent ratio of anion/L-lysine means a value calculated in accordance with the following equation by using L-lysine (L-Lys) content, sulfate ion content, chloride ion content, ammonium ion content, sodium ion content, potassium ion content, magnesium ion content and calcium ion content in the solid matter of the a dry granulated product:

$$\text{equivalent ratio of anion/L-lysine} = (2 \times [SO_4^{2-}] + [Cl^-] - [NH_4^+] - [Na^+] - [K^+] - 2 \times [Mg^{2+}] - 2 \times [Ca^{2+}])/[L\text{-Lys}]$$

where [ ] means a molar concentration.

In order to adjust the equivalent ratio of anion/L-lysine to be within the aforementioned range, for example, hydrochloric acid, sulfuric acid or an L-lysine solution having an equivalent ratio of anion/L-lysine higher than 0.95 may be added to a raw material L-lysine solution having an equivalent ratio of anion/L-lysine lower than 0.68.

Specifically, there can be mentioned a method of neutralizing an L-lysine base solution with an acid, a method of producing L-lysine by fermentation and then adding an L-lysine solution having an equivalent ratio of anion/L-lysine lower than 0.95 to a fermentation solution having an equivalent ratio of anion/L-lysine higher than 0.95, a method of using carbonate as counter ions of L-lysine during the production of L-lysine by fermentation, then granulating and drying a decarboxylated fermentation solution having an equivalent ratio of anion/L-lysine lower than 0.95, and so forth.

The L-lysine solution having an equivalent ratio of anion/L-lysine higher than 0.95 referred to herein means an L-lysine solution having pH in neutral region to acidic region, and for example, a fermentation solution containing L-lysine obtained by a usual fermentation method can be used. Such an L-lysine fermentation solution having an equivalent ratio of anion/L-lysine higher than 0.95 is not suitable for obtaining a dry granulated product having a high L-lysine content. On the other hand, if an L-lysine solution having an equivalent ratio of anion/L-lysine lower than 0.68 is granulated and dried as it is, the product shows marked hygroscopic property and caking property, and thus its handling is difficult. However, if the equivalent ratio of anion/L-lysine of such a solution is adjusted to be within the range of 0.68 to 0.95 by mixing it with an L-lysine fermentation solution having an equivalent ratio of anion/L-lysine higher than 0.95, and then the solution is granulated and dried, a dry granulated product showing low caking property and low hygroscopic property can be obtained.

In order to obtain the dry granulated product of the present invention by the method of neutralizing an L-lysine base solution with acid, for example, the following procedure can be used.

An inorganic acid such as hydrochloric acid or sulfuric acid is added to a raw material L-lysine base solution to prepare a solution of which equivalent ratio of anion/L-lysine is adjusted to be 0.68 to 0.95. Then, the solution after concentration or as it is can be granulated and dried to obtain the dry granulated product of the present invention.

As the raw material L-lysine base solution used in this case, there can be used a solution obtained by loading an L-lysine solution produced by fermentation, chemical synthesis etc. on a cation exchange resin to allow L-lysine to adsorb on the resin, then eluting it with aqueous ammonia and concentrating the obtained L-lysine solution under reduced pressure to remove ammonia.

As the method of producing L-lysine by fermentation, a microorganism having an L-lysine producing ability is cultured in a fermentation medium containing at least one kind of carbon source, at least one kind of nitrogen source, mineral salts, amino acids, vitamins, trace amounts of metal elements etc. During the fermentation, pH is maintained within a neutral range, and sufficient stirring and oxygen are supplied.

By purifying L-lysine using a cation exchange resin from the fermentation solution obtained as described above, an L-lysine solution having an equivalent ratio of anion/L-lysine lower than 0.68 can be obtained.

The microorganism having an L-lysine producing ability is not particularly limited, and any microorganism having an L-lysine producing ability can be used. While examples of the microorganism used include, for example, coryneform bacteria and bacteria belonging to the genus *Escherichia, Serratia* or *Bacillus*, the bacteria used for the method of the present invention are not limited to these bacteria.

Specific examples of *Escherichia coil* strain having L-lysine producing ability include *Escherichia coli* W3110 (tyrA)/pCABD2 (described in International Patent Publication WO95/16042) and so forth. The *Escherichia coli* W3110 (tyrA)/pCABD2 is a strain obtained by introducing a plasmid pCABD2 containing genes encoding enzymes of L-lysine biosynthetic pathway into W3110(tyrA), which is a tyrA deficient strain of *Escherichia coli* (it was designated as AJ12604, deposited at the National Institute of Bioscience and Human-Technology, Agency of Industrial Science and Technology, Ministry of International Trade and Industry (currently, the independent administrative institution, National Institute of Advanced Industrial Science and Technology, International Patent Organism Depositary (Address: postal code 305-8566, Chuo Dai-6, 1-1 Higashi 1-Chome, Tsukuba-shi, Ibaraki-ken, Japan) on Jan. 28, 1991 under an accession number of FERM P-11975, and then converted to an international deposit under the provisions of the Budapest Treaty on Oct. 29, 1987 under an accession number of FERM BP-3579).

The plasmid pCABD2 contains a gene coding for a mutant dihydrodipicolinate synthase of which histidine residue at position 118 is mutated to a tyrosine residue and feedback inhibition by L-lysine is desensitized, gene coding for a mutant aspartokinase III of which threonine residue at position 352 is mutated to an isoleucine residue and feedback inhibition by L-lysine is desensitized, and genes coding for dihydrodipicolinate reductase and diaminopimelate dehydrogenase.

Further, the *E. coli* W3110(tyrA) strain can be obtained as described below. That is, many strains obtained by introducing a plasmid into the W3110(tyrA) strain are disclosed in European Patent Laid-open Publication No. 488424/1992. For example, a strain obtained by introducing a plasmid pHATerm is designated as *E. coli* W3110(tyrA)/pHATerm, and deposited at the National Institute of Bioscience and Human-Technology, Agency of Industrial Science and Technology under an accession number of FERM BP-3653. The W3110(tyrA) strain can be obtained by eliminating the plasmid pHATerm from this *E. coli* W3110(tyrA)/pHATerm strain. Elimination of the plasmid can be performed in a conventional manner.

Examples of L-lysine producing bacteria belonging to the genus *Serratia* include bacteria belonging to the genus *Serratia* transformed by introduction of a DNA coding for dihydrodipicolinate synthase having a mutation that desensitizes feedback inhibition by L-lysine into their cells, and bacteria belonging to the genus *Serratia* containing aspartokinase of which feedback inhibition by L-lysine is desensitized (International Patent Publication WO96/41871).

In the present invention, as the method for obtaining the dry granulated product, a usual method for obtaining a dry granulated product containing L-amino acid can be used without particular limitation. Examples of the method for granulation drying include a method of first solidifying the L-lysine solution described above and granulating the solidified product, a method of directly granulating and drying the solution using a seed, and so forth.

In the former method, as the method for solidifying the L-lysine solution, methods for drying and solidification using a spray dryer, drum dryer, spin flash dryer or the like can be used. The obtained solid containing L-lysine can be granulated by using various granulators such as a granulation mixer, apparatuses for fluidized bed granulation, rolling granulation etc. In this case, if the L-lysine solution having a regulated equivalent ratio of anion/L-lysine is used as a binder for granulation, granulation can be easily attained.

On the other hand, as the method of directly granulating and drying an L-lysine solution using seed particles, there can be used a method of directly drying and granulating an L-lysine solution in which the aforementioned L-lysine containing granulated product is used as the seed particles in the fluidized bed granulation and the L-lysine solution is sprayed into the bed. As the seed particles, the aforementioned L-lysine containing granulated product can be used, and for example, a part of the product obtained by the fluidized bed granulation can be ground and used as the seed particles.

The both methods are carried out so that moisture content in the obtained dried granulated product should become 5% by weight or less.

After the raw material L-lysine solution is produced by fermentation, the dry granulated product of the present invention is obtained, when the method of adding an L-lysine base solution having an equivalent ratio of anion/L-lysine lower than 0.95 is used, as follows. First, the aforementioned L-lysine base solution is added to a fermentation solution in which L-lysine is accumulated to prepare a solution having such a composition that the solution should have a predetermined equivalent ratio of anion/L-lysine. The solution can be granulated and dried after concentration or the solution as it is can be directly granulated and dried to obtain a dry granulated product of the present invention.

For the production of an L-lysine base solution having an equivalent ratio of anion/L-lysine lower than 0.95 by fermentation, the aforementioned method of producing L-lysine by fermentation can be mentioned.

Upon production of the dry granulated product of the present invention, although cells in the culture broth may be removed or may not be removed, it is more advantageous that the cell should be removed, since the removal of the cells improves L-lysine content in the dry granulated product of the present invention. As the method for removing cells from culture broth, centrifugation, filtration, precipitation and so forth can be used.

As the method for granulation drying used in this method, the aforementioned granulation drying methods can also be used.

When the method of using carbonate for counter ions of L-lysine during the production of L-lysine by fermentation and then performing decarboxylation is used, the dry granulated product of the present invention is obtained, for example, as follows.

The fermentation in which a strain having an ability to produce L-lysine is cultured in a medium under an aerobic condition is performed by utilizing carbonate ions or bicarbonate ions as major counter ions of L-lysine, and the obtained fermentation solution is used as a raw material and subjected to decarboxylation to obtain an L-lysine solution having a reduced equivalent ratio of anion/L-lysine. Under preferred conditions, the L-lysine solution obtained as described above should have an equivalent ratio of anion/L-lysine in the range of 0.68 to 0.95. If the equivalent ratio of anion/L-lysine is higher or lower than this range, hydrochloric acid, sulfuric acid or an L-lysine solution having an equivalent ratio of anion/L-lysine higher than 0.95 or lower than 0.68 can be added to the raw material L-lysine solution, as required, to adjust the equivalent ratio of anion/L-lysine to be within the predetermined range.

In the aforementioned method, the microorganism having an L-lysine producing ability is not particularly limited, and any microorganism having an L-lysine producing ability may be used. For example, the microorganisms described above can be mentioned.

When a microorganism having an L-lysine producing ability is cultured in a medium under an aerobic condition in the method of the present invention, specifically, carbonate ions, bicarbonate ions or the both can be used as major counter ions of L-lysine, for example, as follows.

That is, pH of the medium is controlled to be 6.5 to 9.0, preferably 6.5 to 8.0, during the culture and to be 7.2 to 9.0 at the end of the culture. Alternatively, pressure in a fermentation tank is controlled to be positive during the culture, or carbon dioxide or a mixed gas containing carbon dioxide is supplied into the medium so that there should be a culture period where bicarbonate and/or carbonate ions are present in the medium in an amount of 2 g/L or more. The expression "there should be a culture period where bicarbonate and/or carbonate ions are present in the medium in an amount of 2 g/L or more" used herein does not necessarily mean that 2 g/L or more of the ions must exist during the whole culture period, but means that it is sufficient that 2 g/L or more of the ions exist during a certain partial period during the culture period. The period where the ions are present in an amount of 2 g/L or more preferably exists in the period from the logarithmic growth phase to the stationary phase.

In the present invention, if the controlled pH is increased, the equilibrium is changed so that the monovalent anion in the culture broth, $HCO_3^-$, should be converted into a divalent anion, $CO_3^{2-}$, and thus the ion becomes more effective as the counter ion. Furthermore, when pH is controlled with ammonia, increase of pH leads to supply of ammonia, and it can be a nitrogen source of the L-lysine fermentation. As cations other than L-lysine, K, Na, Mg, Ca etc. derived from the medium components are mentioned. These cations constitute 50% or less of the total cations.

In order to obtain positive pressure in a fermentation tank during the fermentation, for example, an intake gas pressure higher than evacuation gas pressure can be used. By using a positive pressure in a fermentation tank, carbon dioxide generated by the fermentation is dissolved in the culture broth to generate bicarbonate or carbonate ions, and these may serve as the counter ions of L-lysine. The pressure in the fermentation tank is specifically 0.03 to 0.2 MPa, preferably 0.05 to 0.15 MPa.

Further, carbon dioxide may be dissolved in the culture broth by supplying carbon dioxide or a mixed gas containing carbon dioxide into the culture broth. Furthermore, the pressure in the fermentation tank may be controlled to be positive while supplying carbon dioxide or a mixed gas containing carbon dioxide into the culture broth.

In order to control the pressure in a fermentation tank to be positive, for example, an intake gas pressure higher than evacuation gas pressure can be used. When carbon dioxide is supplied to the culture broth, for example, carbon dioxide or a mixed gas containing 5 volume % or more of carbon dioxide can be bubbled in the culture broth.

The liquid medium used for the culture is not particularly limited, and conventional known media containing organic and inorganic nutrients such as a carbon source and nitrogen source as well as trace amount nutrients can be suitably used depending on the microorganism used. The carbon source may be any carbon source that can be assimilated by the microorganism. Examples thereof include saccharides such as sucrose, glucose, fructose, molasses and starch hydrolysate, organic acids such as acetic acid and alcohols such as ethanol and methanol. Examples of the nitrogen source include inorganic substances such as ammonium ion, protein hydrolysate and yeast extract. Examples of the trace amount nutrients include amino acids, vitamins and trace amount metal elements.

The fermentation scheme is not also particularly limited, and any of the batch culture in which medium is not additionally fed, feeding culture in which medium is further fed when initially stocked saccharide is consumed and continuous culture in which medium is extracted when the volume of medium exceeds capacity of a fermentation tank may be used.

Although the culture temperature may be suitably selected according to the microorganism used, it is usually 25 to 45° C., preferably 30 to 40° C. Further, sufficient stirring and sufficient oxygen are supplied during the fermentation.

In the conventional methods, a sufficient amount of ammonium sulfate, ammonium chloride, sulfuric acid decomposition product or hydrochloric acid decomposition products of proteins and the like are usually added to the medium in order to use produced L-lysine as counter ions, and sulfate ions and chloride ions provided by these substances are contained in the medium. Therefore, concentration of weakly acidic carbonate ions becomes extremely low level of ppm order during the culture. However, the present invention is characterized by reducing these sulfate ions and chloride ions so that carbon dioxide excreted from microorganisms during the fermentation should be dissolved in the medium to produce counter ions. Therefore, in the present invention, it is unnecessary to add sulfate ions or chloride ions exceeding the amount required for the growth of the microorganism. Preferably, an optimum amount of ammonium sulfate or the like is added to the medium during an early stage of the culture, and the addition is terminated in the course of the culture. Alternatively, ammonium sulfate or the like may be added while maintaining the balance with the amount of carbonate ions or bicarbonate ions dissolved in the medium. Further, ammonia may be added to the medium as a nitrogen source of L-lysine.

If ammonium sulfate is added to the medium as a source of counter ions of L-lysine, carbon dioxide in the culture broth is usually eliminated by the sulfate ions. In contrast, in the present invention, an excessive amount of ammonium sulfate need not be added to the medium, and therefore carbon dioxide can be easily dissolved in the fermentation solution.

The fermentation solution containing L-lysine obtained by the present invention contains 5 to 80% of carbonate ions or bicarbonate ions with respect to the normality of L-lysine produced by fermentation. These carbonate ions or bicarbonate ions are easily eliminated as carbon dioxide if heat is applied, the culture broth is placed under a reduced pressure condition, or the culture broth is heated under a reduced pressure condition. As a result, the content of L-lysine in the solid matter in the fermentation solution is increased. The heating temperature may be 40° C. or more, preferably 60° C. to 90° C. The reduced pressure may be 600 kPa or less, preferably 0.04 MPa to 0.2 MPa.

This results in reduction of the equivalent ratio of anion/L-lysine in the culture broth to 0.20 to 0.95. These remaining counter ions consist of sulfate ions and chloride ions added to the medium.

Then, the equivalent ratio of anion/L-lysine is adjusted to 0.68 to 0.95 by adding an inorganic acid such as hydrochloric acid and sulfuric acid or an L-lysine solution having an equivalent ratio of anion/L-lysine higher than 0.95.

After the equivalent ratio of anion/L-lysine is adjusted, the L-lysine solution can be granulated and dried to obtain a dry granulated product. Also in this granulation drying method, the aforementioned granulation drying methods can be used.

According to the present invention, an L-lysine containing dried granulated product containing L-lysine at a higher concentration and showing favorable hygroscopic property and caking property can be obtained.

EXAMPLES

Hereafter, the present invention will be explained more specifically with reference to the following examples.

Example 1

Equivalent ratio of anion/L-lysine of a raw material L-lysine base solution was adjusted by using sulfuric acid, and a dry granulated product was produced.

Fermentation was performed by using an L-lysine producing bacterium, *Escherichia coli* W3110(tyrA)/pCABD2 (International Patent Publication WO95/16042) in a medium having the following composition.

Glucose 100 g/L, ammonium sulfate 60 g/L, $KH_2PO_4$ 1 g/L, $MgSO_4 \cdot 7H_2O$ 0.4 g/L, $FeSO_4 \cdot 7H_2O$ 10 mg/L, $MnSO_4 \cdot 4H_2O$ 8.1 mg/L, biotin 300 μg/L, thiamin hydrochloride 200 μg/L, soybean protein hydrolysate (total nitrogen content: 3.2%) 35 ml/L, L-methionine 200 mg/L, calcium carbonate 50 g/L, pH 7.0

The L-lysine producing strain was inoculated to the aforementioned medium and cultured at 36° C. for 72 hours. After completion of the culture, 10 L of culture broth containing L-lysine was obtained.

The culture broth was adjusted to pH 3.0 with addition of sulfuric acid and then loaded on a cation exchange resin, DIAION SK1BL (Mitsubishi Chemical) so that L-lysine should be adsorbed on the resin. After the adsorption of L-lysine, the resin was washed with water, and L-lysine was eluted with aqueous ammonia. The eluent containing L-lysine was then concentrated in a rotatry evaporator until L-lysine concentration became 50% by weight to obtain an L-lysine base solution.

Then, sulfuric acid (98%, regent of special grade) was added to the L-lysine base solution to adjust the equivalent ratio of anion/L-lysine to be 0.6984. Thus, a granulation drying feed solution was obtained.

A part of the granulation drying feed solution in a volume of 1 L was dried by using a spray dryer (Pulvis GB22, Yamato Scientific) to obtain powder. The obtained powder as seed particles and the remaining granulation drying feed solution that was not used in the drying in the spray dryer as a binder solution were fed to a granulation dryer (SPIR-A-FLOW, Freund), and granulation drying was performed to obtain a dry granulated product.

Example 2

Equivalent ratio of anion/L-lysine of a raw material L-lysine base solution was adjusted by using hydrochloric acid, and a dry granulated product was produced.

Hydrochloric acid (36%, regent of special grade) was added to an L-lysine base solution obtained in the same manner as in Example 1 to adjust the equivalent ratio of anion/L-lysine to be 0.6903. Then, granulation drying was performed in the same manner as in Example 1 to obtain a dry granulated product.

Comparative Example 1

Granulation drying was performed in the same manner as in Example 1 by using an L-lysine base solution obtained in the same manner as in Example 1 as a raw material without adjusting the equivalent ratio of anion/L-lysine to obtain a dry granulated product.

Comparative Example 2

Sulfuric acid was added to an L-lysine base solution obtained in the same manner as in Example 1 to adjust the equivalent ratio of anion/L-lysine to be 0.9622. Then, granulation drying was performed in the same manner as in Example 1 to obtain a dry granulated product.

L-Lysine content and equilibrium moisture content of the obtained dried granulated products were measured, and the products were evaluated for caking property.

As for the measurement of the equilibrium moisture content, a moisture content of each product after storage in environments of different relative humidities for 7 days under a temperature condition of 25° C. was used as the equilibrium moisture content. As for the evaluation of the caking property, a sample sieved beforehand to contain particles having a diameter of 425 μm to 600 μm was placed into a styrol bottle having a diameter of 37 mm and stored in environments of different relative humidities for 7 days under a temperature condition of 25° C. Then, the caking property was evaluated according to the following evaluation criteria. The results are shown in Tables 1 to 3.

⊚: Sample flows only by leaning a container.
◯: If impact is lightly given once, sample flows.
Δ: If impact is given several times, sample begins to flow.
X: If impact is given continuously, sample begins to flow.
XX: Even if impact is given continuously, blocks remain.

TABLE 1

L-Lys content

|  | Comparative Example 1 | Example 1 | Example 2 | Comparative Example 2 |
|---|---|---|---|---|
| Anion/L-lysine ratio | −0.0133 | 0.6984 | 0.6903 | 0.9622 |
| L-Lys content | 94% | 72% | 83.2% | 67% |

TABLE 2

Result of equilibrium moisture content measurement

|  | Comparative Example 1 | Example 1 | Example 2 | Comparative Example 2 |
|---|---|---|---|---|
| Anion/L-lysine ratio | −0.0133 | 0.6984 | 0.6903 | 0.9622 |
| Relative humidity 33% | 5.9% | 3.00% | 0.69% | 2.88% |
| Relative humidity 43% | 6.5% | 4.24% | 1.00% | 3.46% |
| Relative humidity 58% | 8.5% | 7.95% | 1.23% | 5.76% |
| Relative humidity 65% | 14.9% | 10.87% | 4.53% | 8.12% |

TABLE 3

Result of evaluation of caking property

|  | Comparative Example 1 | Example 1 | Example 2 | Comparative Example 2 |
|---|---|---|---|---|
| Anion/L-lysine ratio | −0.0133 | 0.6984 | 0.6903 | 0.9622 |
| Relative humidity 33% | XX | ⊚ | ⊚ | ⊚ |
| Relative humidity 43% | XX | ⊚ | ◯ | ⊚ |

TABLE 3-continued

| | Result of evaluation of caking property | | | |
|---|---|---|---|---|
| | Comparative Example 1 | Example 1 | Example 2 | Comparative Example 2 |
| Relative humidity 58% | XX | ○ | ○ | ○ |
| Relative humidity 65% | XX | ○ | Δ | ○ |

It can be seen that, in Example 1 where the equivalent ratio of anion/L-lysine was adjusted to 0.6984, the hygroscopic property and caking property were not degraded, and the L-lysine content was improved compared with Comparative Example 2. Further, in Comparative Example 1, although the L-lysine content is improved compared with Example 1, the hygroscopic property was strong, the caking property is also markedly degraded, and thus storage stability could not be secured. Therefore, it can be judged that the dry granulated product of Example 1 is superior when the L-lysine content, hygroscopic property and caking property are evaluated together.

Further, also in Example 2 where the equivalent ratio of anion/L-lysine was adjusted to 0.6903, it could be confirmed that the hygroscopic property and caking property were not degraded, and the L-lysine content was improved compared with Comparative Example 2.

Example 3

Equivalent ratio of anion/L-lysine of an L-lysine fermentation solution was adjusted by using an L-lysine base solution, and a dry granulated product was produced.

L-Lysine was produced by the same fermentation method as in Example 1 described above. The culture broth was centrifuged to precipitate cells to obtain a supernatant. Then, the supernatant was concentrated in a rotary evaporator (EYELA ROTARY VACUUM EVAPORATOR N-3NW) until the concentration of solid matter became 55%.

Further, to the above concentrate, a concentrated L-lysine base solution produced in the same manner as in Example 1 was added so that the equivalent ratio of anion/L-lysine should become 0.8383. The obtained solution was used as a granulation drying feed solution.

A part of the granulation drying feed solution in a volume of 1 L was dried by using a spray dryer (Pulvis GB22, Yamato Scientific) to obtain powder. The obtained powder as seed particles and the remaining granulation drying feed solution that was not used in the drying in the spray dryer as a binder solution were fed to a granulation dryer (SPIR-A-FLOW, Freund), and granulation drying was performed to obtain a dry granulated product.

Comparative Example 3

After performing fermentation, removal of cells and concentration in the same manner as in Example 3, the concentrate was added with an L-lysine base solution produced in the same manner as in Example 1 so that the equivalent ratio of anion/L-lysine of the concentrate should become 0.4302 and used as a granulation drying feed solution. Then, the granulation drying was performed in the same manner as in Example 1 to obtain a dry granulated product.

Comparative Example 4

After performing fermentation, removal of cells and concentration in the same manner as in Example 3, the obtained concentrate was used for granulation drying without adjusting the equivalent ratio of anion/L-lysine. The equivalent ratio of anion/L-lysine of the dry granulated product was 1.0772.

The lysine contents as well as the results of equilibrium moisture content measurement and evaluation of caking property of the dry granulated products obtained in Example 3, Comparative Examples 3 and 4 are shown in Tables 4 to 6.

TABLE 4

| | L-Lys content | | |
|---|---|---|---|
| | Comparative Example 3 | Example 3 | Comparative Example 4 |
| Anion/L-lysine ratio | 0.4302 | 0.8383 | 1.0772 |
| L-Lys content | 79% | 69% | 64% |

TABLE 5

| | Result of equilibrium moisture content measurement | | |
|---|---|---|---|
| | Comparative Example 3 | Example 3 | Comparative Example 4 |
| Anion/L-lysine ratio | 0.4302 | 0.8383 | 1.0772 |
| Relative humidity 33% | 3.1% | 2.78% | 3.28% |
| Relative humidity 43% | 3.8% | 3.39% | 3.99% |
| Relative humidity 58% | 5.1% | 5.78% | 6.98% |
| Relative humidity 65% | 11.9% | 8.15% | 10.12% |

TABLE 6

| | Result of evaluation of caking property | | |
|---|---|---|---|
| | Comparative Example 3 | Example 3 | Comparative Example 4 |
| Anion/L-lysine ratio | 0.4302 | 0.8383 | 1.0772 |
| Relative humidity 33% | ◎ | ◎ | ◎ |
| Relative humidity 43% | Δ | ◎ | Δ |
| Relative humidity 58% | XX | ○ | X |
| Relative humidity 65% | XX | ○ | X |

It can be seen that the product of Example 3 had a lower equilibrium moisture content and lower hygroscopic property, although it had a lower L-lysine content, compared with the product of Comparative Example 3. The caking property of the product of Example 3 was also more favorable compared with the product of Comparative Example 3.

Furthermore, the product of Example 3 had characteristics of a higher L-lysine content, lower hygroscopic property and lower caking property compared with the product of Comparative Example 4.

Example 4

Adjustment of equivalent ratio of anion/L-lysine by fermentation conditions (1)

(1) Seed Culture of L-Lysine Producing Bacterium

A medium containing 45 g/L of glucose, 15 g/L of molasses, 2 g/L (as nitrogen) of soybean protein hydrolysate, 2 g/L of $KH_2PO_4$, 5.6 g/L of NaOH, 10 g/L of ammonium sulfate, 0.8 g/L of $MgSO_4.7H_2O$, 20 mg/L of $FeSO_4.7H_2O$, 20 mg/L of $MnSO_4.4H_2O$, 0.8 mg/L of thiamin hydrochloride and 0.2 mg/L of biotin (pH 6.0) was introduced into 1-L volume small glass fermentation tank in a volume of 300 mL and sterilized by heating at 120° C. for 20 minutes. After the fermentation tank was cooled to 31.5° C., 5 platinum loops of *Brevibacterium lactofermentum* ATCC 31269 (refer to U.S. Pat. No. 4,066,501) preliminarily grown on an LB plate for 24 hours was inoculated to the medium and cultured at 31.5° C. and pH 7.0 for 30 hours with sufficient aeration and stirring.

(2) Main Culture

A medium containing 30 g/L of glucose, 45 g/L of molasses, 2 g/L (as nitrogen) of soybean protein hydrolysate, 1.4 g/L of phosphoric acid, 1.2 g/L of NaOH, 30 g/L of ammonium sulfate, 1.5 g/L of $MgSO_4.7H_2O$, 15 mg/L of $FeSO_4.7H_2O$, 15 mg/L of $MnSO_4.4H_2O$, 5 mg/L of thiamin hydrochloride and 0.75 mg/L of biotin (pH 5.0) was introduced into 1-L volume small glass fermentation tank in a volume of 300 mL and sterilized by heating at 120° C. for 20 minutes. After the fermentation tank was cooled to 31.5° C., 45 mL of the above seed culture was inoculated to the medium, and culture was performed at 34° C. with aeration of ½ vvm and sufficient stirring.

After a predetermined amount of the feed medium shown below was fed to the culture broth, the culture was finished when the saccharide in the culture broth was fully consumed. The culture was started at pH 7.0, and pH was gradually changed to 8.0. Simultaneously, the pressure in the tank was changed from 0 to 0.12 MPa.

[Feed Medium]

Medium containing 530 g/L of glucose, 1.4 g/L (as nitrogen) of soybean protein hydrolysate, 1.0 g/L of KOH, 44 g/L of ammonium chloride, 0.3 g/L of $MgSO_4.7H_2O$, 0.35 mg/L of thiamin hydrochloride and 0.35 mg/L of biotin (pH 5.5)

After completion of the culture, the fermentation solution had an equivalent ratio of anion/L-lysine of 0.7518.

The culture broth was centrifuged to precipitate the cells to obtain a supernatant, and the obtained supernatant was concentrated in a rotary evaporator (EYELA ROTARY VACUUM EVAPORATOR N-3NW) until the concentration of solid matter became 55%.

Then, a half volume of the concentrated solution was spray-dried by using a spray dryer (Pulvis GB22, Yamato Scientific). The obtained powder as seed particles and the remaining concentrated solution that was not used in the drying in the spray dryer as a binder solution were fed to a granulation dryer (SPIR-A-FLOW, Freund), and granulation drying was performed to obtain a dry granulated product.

The lysine contents as well as the results of equilibrium moisture content measurement and evaluation of caking property of the dry granulated products obtained in Example 4, Comparative Examples 3 and 4 are shown in Tables 7 to 9.

TABLE 7

L-Lys content

|  | Comparative Example 3 | Example 4 | Comparative Example 4 |
|---|---|---|---|
| Anion/L-lysine ratio | 0.4302 | 0.7518 | 1.0772 |
| L-Lys content | 79% | 73% | 64% |

TABLE 8

Result of equilibrium moisture content measurement

|  | Comparative Example 3 | Example 4 | Comparative Example 4 |
|---|---|---|---|
| Anion/L-lysine ratio | 0.4302 | 0.7518 | 1.0772 |
| Relative humidity 33% | 3.1% | 3.53% | 1.45% |
| Relative humidity 43% | 3.8% | 4.91% | 1.93% |
| Relative humidity 58% | 5.1% | 9.56% | 4.08% |
| Relative humidity 65% | 11.9% | 12.42% | 6.36% |

TABLE 9

Result of evaluation of caking property

|  | Comparative Example 3 | Example 4 | Comparative Example 4 |
|---|---|---|---|
| Anion/L-lysine ratio | 0.4302 | 0.7518 | 1.0772 |
| Relative humidity 33% | ◎ | ◎ | ◎ |
| Relative humidity 43% | Δ | ◯ | Δ |
| Relative humidity 58% | XX | Δ | X |
| Relative humidity 65% | XX | X | XX |

The dry granulated product obtained in Example 4 had a higher L-lysine content compared with the product of Comparative Example 4. Further, although the product of Example 4 had a slightly higher equilibrium moisture content, it showed low caking property, and it is considered to cause no problem in practical use.

Further, although the dry granulated product of Example 4 had a lower L-lysine content compared with the product of Comparative Example 3, the product of Example 4 did not show notable caking property even under a condition of 58% relative humidity, whereas the product of Comparative Example 3 showed strong caking property.

Example 5

Adjustment of equivalent ratio of anion/L-lysine by fermentation conditions (2)

(1) Seed Culture of L-Lysine Producing Bacterium

A medium containing 40 g/L of glucose, 0.6 g/L (as nitrogen) of soybean protein hydrolysate, 1 g/L of $KH_2PO_4$, 5.6 g/L of NaOH, 1.0 g/L of ammonium sulfate, 10 mg/L of $FeSO_4.7H_2O$ and 10 mg/L of $MnSO_4.4H_2O$ (pH 6.0) was introduced into 1-L volume small glass fermentation tank in a volume of 300 mL and sterilized by heating at 120° C. for 20 minutes. After the fermentation tank was cooled to 31.5° C., 5 platinum loops of *Escherichia coli* W3110(tyrA)/pCABD2 (International Patent Publication WO95/16042) preliminarily grown on an LB plate for 24 hours was inoculated to the medium and cultured at 37° C. and pH 6.7 for 24 hours with sufficient aeration and stirring.

(2) Main Culture

A medium containing 30 g/L of glucose, 0.4 g/L (as nitrogen) of soybean protein hydrolysate, 0.5 g/L of $KH_2PO_4$, 20 g/L of ammonium sulfate, 1.0 g/L of $MgSO_4.7H_2O$, 30 mg/L of $FeSO_4.7H_2O$ and 30 mg/L of $MnSO_4.4H_2O$ (pH 5.0) was introduced into 1-L volume small glass fermentation tank in a volume of 300 mL and sterilized by heating at 120° C. for 20 minutes. After the fermentation tank was cooled to 31.5° C., 50 mL of the above seed culture was inoculated to the medium, and culture was performed at 34° C. with aeration of ½ vvm and sufficient stirring.

When the saccharide concentration in the culture broth became 5 g/L or less, a solution containing 760 g/L of glucose was fed by the method described in Japanese Patent Laid-open Publication No. 5-30985 in the same manner as in Example 1. Specifically, pH and dissolved oxygen concentration were measured to detect depletion status of the carbon source based on changes of the measured values, and the medium was fed so as to maintain the concentration of the carbon source in the culture broth to be 5 g/L or less.

After a predetermined amount of the feed medium was fed, the culture was finished when the saccharide in the culture broth was fully consumed. The culture was started at pH 6.7, and pH was gradually changed to 8.0. Simultaneously, the pressure in the tank was changed from 0 to 0.1 MPa.

After completion of the culture, the fermentation solution had an equivalent ratio of anion/L-lysine of 0.8574.

The culture broth was centrifuged to precipitate and separate the cells, and the obtained supernatant was concentrated in a rotary evaporator (EYELA ROTARY VACUUM EVAPORATOR N-3NW) until the concentration of solid matter became 55%. Then, a half volume of the concentrated solution was spray-dried by using a spray dryer (Pulvis GB22, Yamato Scientific). The obtained powder as seed particles and the remaining concentrated solution that was not used in the drying in the spray dryer as a binder solution were fed to a granulation dryer (SPIR-A-FLOW, Freund), and granulation drying was performed to obtain a dry granulated product.

The lysine contents as well as the results of equilibrium moisture content measurement and evaluation of caking property of the dry granulated products obtained in Example 5, Comparative Examples 3 and 4 are shown in Tables 10 to 12.

TABLE 10

| L-Lys content | | | |
|---|---|---|---|
| | Comparative Example 3 | Example 5 | Comparative Example 4 |
| Anion/L-lysine ratio | 0.4302 | 0.8574 | 1.0772 |
| L-Lys content | 79% | 70% | 64% |

TABLE 11

| Result of equilibrium moisture content measurement | | | |
|---|---|---|---|
| | Comparative Example 3 | Example 5 | Comparative Example 4 |
| Anion/L-lysine ratio | 0.4302 | 0.8574 | 1.0772 |
| Relative humidity 33% | 3.1% | 2.94% | 1.45% |
| Relative humidity 43% | 3.8% | 4.01% | 1.93% |
| Relative humidity 58% | 5.1% | 7.78% | 4.08% |
| Relative humidity 65% | 11.9% | 10.23% | 6.36% |

TABLE 12

| Result of evaluation of caking property | | | |
|---|---|---|---|
| | Comparative Example 3 | Example 5 | Comparative Example 4 |
| Anion/L-lysine ratio | 0.4302 | 0.8574 | 1.0772 |
| Relative humidity 33% | ◎ | ◎ | ◎ |
| Relative humidity 43% | Δ | ○ | Δ |
| Relative humidity 58% | XX | ○ | X |
| Relative humidity 65% | XX | Δ | XX |

The dry granulated product obtained in Example 5 had a higher L-lysine content compared with the product of Comparative Example 4. Further, although the product of Example 4 showed slightly stronger hygroscopic property evaluated based on the equilibrium moisture content, it conversely showed favorable caking property.

Further, although the product of Example 5 had a lower L-lysine content compared with the product of Comparative Example 3, it showed favorable flowability even under a condition of 58% relative humidity, whereas the product of Comparative Example 3 showed strong caking property.

What we claim is:

1. A method for preparing a dry granulated product containing L-lysine, comprising the steps of culturing a microorganism having an ability to produce L-lysine in a liquid medium under an aerobic condition to produce and accumulate L-lysine in the medium and obtaining the dry granulated product from the medium, wherein the culture is performed to obtain a fermentation solution containing L-lysine, while pH of the medium is controlled to be 6.5 to 9.0 during the culture and to be 7.2 to 9.0 at the end of the culture, and pressure in a fermentation tank is controlled to be positive during the culture to dissolve carbon dioxide into the medium, or carbon dioxide or a mixed gas containing carbon dioxide is supplied into the medium, so that there should be a culture period where bicarbonate and/or carbonate ions are present in the medium in an amount of 2 g/L or more, adding hydrochloric acid, sulfuric acid or an L-lysine solution having an equivalent ratio of anion/L-lysine higher than 0.95 to the fermentation solution so that the fermentation solution should have an equivalent ratio of anion/L-lysine in the range of 0.68 to 0.95, and the fermentation solution is concentrated under reduced pressure, and the obtained concentrate is granulated and dried to obtain a dry granulate product containing L-lysine and having the following composition:

L-lysine content in solid matter: 40 to 85% by weight;
equivalent ratio of anion/L-lysine: 0.68 to 0.95;
moisture content: 5% by weight or less;
wherein the equivalent ratio of anion/L-lysine is a value calculated in accordance with the following equation by using L-lysine (L-Lys) content, sulfate ion content, chloride ion content, ammonium ion content, sodium ion content, potassium ion content, magnesium ion content and calcium ion content in the solid matter of the dry granulate product:

$$\text{equivalent ratio of anion/L-lysine}=(2\times[SO_4^{2-}]+[Cl^-]-[NH_4^+]-[Na^+]-[K^+]-2\times[Mg^{2+}]-2\times[Ca^{2+}])/[\text{L-Lys}];$$

where [ ] means a molar concentration.

2. The method according to claim 1, wherein the L-lysine solution having an equivalent ratio of anion/L-lysine higher than 0.95 is a fermentation solution in which L-lysine is accumulated.

3. The method according to claim 1, wherein hydrochloric acid is added to the fermentation solution so that the fermentation solution has an equivalent ratio of anion/L-lysine in the range of 0.68 to 0.95.

4. The method according to claim 1, wherein sulfuric acid is added to the fermentation solution so that the fermentation solution has an equivalent ratio of anion/L-lysine in the range of 0.68 to 0.95.

5. The method according to claim 1, wherein an L-lysine solution having an equivalent ratio of anion/L-lysine higher than 0.95 is added to the fermentation solution so that the fermentation solution has an equivalent ratio of anion/L-lysine in the range of 0.68 to 0.95.

* * * * *